(12) United States Patent
Tanaka

(10) Patent No.: US 11,564,365 B2
(45) Date of Patent: Jan. 31, 2023

(54) SPINACH AND METHOD FOR PRODUCING THE SAME

(71) Applicant: SAKATA SEED CORPORATION, Yokohama (JP)

(72) Inventor: Hideto Tanaka, Yokohama (JP)

(73) Assignee: SAKATA SEED CORPORATION, Yokohama (JP)

( * ) Notice: Subject to any disclaimer, the term of this patent is extended or adjusted under 35 U.S.C. 154(b) by 203 days.

(21) Appl. No.: 17/011,491

(22) Filed: Sep. 3, 2020

(65) Prior Publication Data

US 2020/0396932 A1    Dec. 24, 2020

Related U.S. Application Data

(63) Continuation-in-part of application No. 15/293,639, filed on Oct. 14, 2016, now abandoned.

(30) Foreign Application Priority Data

Oct. 15, 2015    (JP) ................. 2015-203506

(51) Int. Cl.
*A01H 6/02* (2018.01)
*A01H 5/12* (2018.01)

(52) U.S. Cl.
CPC .............. *A01H 6/028* (2018.05); *A01H 5/12* (2013.01)

(58) Field of Classification Search
CPC ................. A01H 6/028; A01H 5/12
See application file for complete search history.

(56) References Cited

U.S. PATENT DOCUMENTS

2017/0105382 A1*  4/2017  Tanaka .............. A01H 5/12

OTHER PUBLICATIONS

Vroemen, Casper W., et al. "The CUP-SHAPED COTYLEDON3 gene is required for boundary and shoot meristem formation in *Arabidopsis*." The Plant Cell 15.7 (2003): 1563-1577 (Year: 2003).*
Hibara, Ken-ichiro, et al. "*Arabidopsis* CUP-SHAPED COTYLE- DON3 regulates postembryonic shoot meristem and organ boundary formation." The Plant Cell 18.11 (2006): 2946-2957. (Year: 2006).*
Laufs, Patrick, et al. "MicroRNA regulation of the CUC genes is required for boundary size control in *Arabidopsis* meristems." (2004): 4311-4322. (Year: 2004).*
Song, Y-G., et al. "Involvement of histone modification in regulating CUP-SHAPED COTYLEDON genes during shoot regeneration in *Arabidopsis*." Biologia plantarum 61.1 (2017): 197-200 (Year: 2017).*
Noh, S. W., Seo, R. R., Park, H. J., & Jung, H. W. (2021). Two *Arabidopsis* Homologs of Human Lysine-Specific Demethylase Function in Epigenetic Regulation of Plant Defense Responses. Frontiers in plant science, 12, 688003. (Year: 2021).*

(Continued)

*Primary Examiner* — Weihua Fan
(74) *Attorney, Agent, or Firm* — Lucas & Mercanti, LLP

(57) ABSTRACT

The object of the present invention is to provide a spinach line with the novel feature of solid petioles at harvest time. As a result of developing many progeny lines having petioles in which the hollow portion is relatively small over many years, a spinach line having solid petioles at harvest time was constructed.

14 Claims, 5 Drawing Sheets
(4 of 5 Drawing Sheet(s) Filed in Color)

Specification includes a Sequence Listing.

Accela     Test cross D

(56) References Cited

OTHER PUBLICATIONS

Qian Wei et al., "Research Progress on Genetic Breeding of Spinach", China Vegetables, Issue 3, Dec. 2014, pp. 5-13, with English Translation.

Sakata Seed Corporation, "Feature of vegetables in summer and autumn in 2013: Passion in Seed", Catalog, 2013, pp. 51-53, with English translation.

Vincent E. Rubatzky, et al., "21. Spinach, Table Beets, and Other Vegetable Chenopods", World Vegetables Principles, Production, and Nutritive Values, Second Edition, 1997, pp. 457-463, including cover and back pages.

Hallavant, Charlotte, et al., "The first archaeobotanical evidence of *Spinacia oleracea* L. (spinach) in late 12th-mid 13th century A.D. France", Veget Hist Archaeobot 23(2): 153-65 (2014).

Irish, B.M., et al., "Characterization of a resistance locus (Pfs-1) to the spinach downy mildew pathogen *Peronospora farinosa* f. sp. *spinaciae*) and development of a molecular marker linked to Pfs-1", Phytopath 90(8):894-900 (2008).

Rural Culture Association, Encyclopedia of Agricultural Techniques, Chapter of Vegetables, vol. 7, Spinach (Basic edition-Spinach: Vegetal characteristics), 1981,pp. 4-7, see concise explanation of relevance and specification page 1, [0004].

Sumio Ohta, Kaneko Seeds, Co., Ltd., "Kaneko Hybrid Sun Power", New variety of vegetables, vol. 15, 2003 edition, Dover, p. 119, and back cover, along with partial English translation (5 pages).

Toei Sotamaru, Sakata Seed Corporation, "Sakata Hybrid Orion", New variety of vegetables, vol. 10, 1988 edition, Dover, p. 135, and p. 239, along with partial English translation (5 pages).

Takii & Co., Ltd, "Let's eat spinach deliciously", Flour and Vegetable Magazine, Oct. 2013, pp. 9-11, with English translation.

Shenxiawang, "Spinach with high temperature resistance, disease-resistant, round leaf, black leaf, and solid rod", Seedling World, Shangqing, Jul. 18, 2014, vol. 15, No. 31, with English translation (2 pages).

Takii & Co., Ltd, "Bentenmaru", Frontline of TAKII Magazine, Autumn Edition, 2012, pp. 3-4, with English translation.

Takii & Co., Ltd, "Best Crop Season of Bentenmaru", Frontline of TAKII Magazine, Autumn Edition, 2013, pp. 15-16, with English translation.

* cited by examiner

Test cross D

Riviera

Accela　　　Test cross D

Accela　　　　　　　　　　　　　Test cross D

```
                        SEQUENCE LISTING

<160> NUMBER OF SEQ ID NOS: 28

<210> SEQ ID NO 1
<211> LENGTH: 42
<212> TYPE: DNA
<213> ORGANISM: Artificial
<220> FEATURE:
<223> OTHER INFORMATION: Synthetic DNA

<400> SEQUENCE: 1
gaaggtgacc aagttcatgc tgcaacacgt cgactaatcc ac              42

<210> SEQ ID NO 2
<211> LENGTH: 42
<212> TYPE: DNA
<213> ORGANISM: Artificial
<220> FEATURE:
<223> OTHER INFORMATION: Synthetic DNA

<400> SEQUENCE: 2
gaaggtcgga gtcaacggat tgcaacacgt cgactaatcc at              42

<210> SEQ ID NO 3
<211> LENGTH: 21
<212> TYPE: DNA
<213> ORGANISM: Artificial
<220> FEATURE:
<223> OTHER INFORMATION: Synthetic DNA

<400> SEQUENCE: 3
gaacctgttg caatgttcgg t                                     21

<210> SEQ ID NO 4
<211> LENGTH: 44
<212> TYPE: DNA
<213> ORGANISM: Artificial
<220> FEATURE:
<223> OTHER INFORMATION: Synthetic DNA

<400> SEQUENCE: 4
gaaggtgacc aagttcatgc tcgtcgccaa tacactaaca tgaa            44

<210> SEQ ID NO 5
<211> LENGTH: 44
<212> TYPE: DNA
<213> ORGANISM: Artificial
<220> FEATURE:
<223> OTHER INFORMATION: Synthetic DNA

<400> SEQUENCE: 5
gaaggtcgga gtcaacggat tcgtcgccaa tacactaaca tgag            44

<210> SEQ ID NO 6
<211> LENGTH: 21
<212> TYPE: DNA
<213> ORGANISM: Artificial
<220> FEATURE:
<223> OTHER INFORMATION: Synthetic DNA

<400> SEQUENCE: 6
caggtgaaca aaccgcatca t                                     21
```

<210> SEQ ID NO 7
<211> LENGTH: 43
<212> TYPE: DNA
<213> ORGANISM: Artificial
<220> FEATURE:
<223> OTHER INFORMATION: Synthetic DNA

<400> SEQUENCE: 7
gaaggtgacc aagttcatgc tccacgacca cttaaaactg tca          43

<210> SEQ ID NO 8
<211> LENGTH: 43
<212> TYPE: DNA
<213> ORGANISM: Artificial
<220> FEATURE:
<223> OTHER INFORMATION: Synthetic DNA

<400> SEQUENCE: 8
gaaggtcgga gtcaacggat tccacgacca cttaaaactg tcg          43

<210> SEQ ID NO 9
<211> LENGTH: 21
<212> TYPE: DNA
<213> ORGANISM: Artificial
<220> FEATURE:
<223> OTHER INFORMATION: Synthetic DNA

<400> SEQUENCE: 9
gaacagagag ggaaaggacg g                                  21

<210> SEQ ID NO 10
<211> LENGTH: 46
<212> TYPE: DNA
<213> ORGANISM: Artificial
<220> FEATURE:
<223> OTHER INFORMATION: Synthetic DNA

<400> SEQUENCE: 10
gaaggtgacc aagttcatgc ttgcctgtga gtatttctta aacgta       46

<210> SEQ ID NO 11
<211> LENGTH: 46
<212> TYPE: DNA
<213> ORGANISM: Artificial
<220> FEATURE:
<223> OTHER INFORMATION: Synthetic DNA

<400> SEQUENCE: 11
gaaggtcgga gtcaacggat ttgcctgtga gtatttctta aacgtt       46

<210> SEQ ID NO 12
<211> LENGTH: 24
<212> TYPE: DNA
<213> ORGANISM: Artificial
<220> FEATURE:
<223> OTHER INFORMATION: Synthetic DNA

<400> SEQUENCE: 12
tggagccaga aaatttagga gttg                               24

<210> SEQ ID NO 13
<211> LENGTH: 47
<212> TYPE: DNA
<213> ORGANISM: Artificial
<220> FEATURE:
<223> OTHER INFORMATION: Synthetic DNA

```
<400> SEQUENCE: 13
gaaggtgacc aagttcatgc tcccttaaga tcatctgagt tcatctg            47

<210> SEQ ID NO 14
<211> LENGTH: 47
<212> TYPE: DNA
<213> ORGANISM: Artificial
<220> FEATURE:
<223> OTHER INFORMATION: Synthetic DNA

<400> SEQUENCE: 14
gaaggtcgga gtcaacggat tcccttaaga tcatctgagt tcatctc            47

<210> SEQ ID NO 15
<211> LENGTH: 21
<212> TYPE: DNA
<213> ORGANISM: Artificial
<220> FEATURE:
<223> OTHER INFORMATION: Synthetic DNA

<400> SEQUENCE: 15
tcagaggcaa agaaaacgct g                                        21

<210> SEQ ID NO 16
<211> LENGTH: 44
<212> TYPE: DNA
<213> ORGANISM: Artificial
<220> FEATURE:
<223> OTHER INFORMATION: Synthetic DNA

<400> SEQUENCE: 16
gaaggtgacc aagttcatgc ttgtagctcc cataaattta gggc               44

<210> SEQ ID NO 17
<211> LENGTH: 44
<212> TYPE: DNA
<213> ORGANISM: Artificial
<220> FEATURE:
<223> OTHER INFORMATION: Synthetic DNA

<400> SEQUENCE: 17
gaaggtcgga gtcaacggat ttgtagctcc cataaattta ggga               44

<210> SEQ ID NO 18
<211> LENGTH: 21
<212> TYPE: DNA
<213> ORGANISM: Artificial
<220> FEATURE:
<223> OTHER INFORMATION: Synthetic DNA

<400> SEQUENCE: 18
agctaattct gagccaaggc c                                        21

<210> SEQ ID NO 19
<211> LENGTH: 46
<212> TYPE: DNA
<213> ORGANISM: Artificial
<220> FEATURE:
<223> OTHER INFORMATION: Synthetic DNA

<400> SEQUENCE: 19
gaaggtgacc aagttcatgc tgttcaataa ctcctgattc tgcaac             46

<210> SEQ ID NO 20
```

<211> LENGTH: 46
<212> TYPE: DNA
<213> ORGANISM: Artificial
<220> FEATURE:
<223> OTHER INFORMATION: Synthetic DNA

<400> SEQUENCE: 20
gaaggtcgga gtcaacggat tgttcaataa ctcctgattc tgcaat    46

<210> SEQ ID NO 21
<211> LENGTH: 21
<212> TYPE: DNA
<213> ORGANISM: Artificial
<220> FEATURE:
<223> OTHER INFORMATION: Synthetic DNA

<400> SEQUENCE: 21
cacaagaaca tgccgtgact g    21

<210> SEQ ID NO 22
<211> LENGTH: 201
<212> TYPE: DNA
<213> ORGANISM: Spinacia oleracea

<400> SEQUENCE: 22
tatctcttgt cggtttgttc aattactttg aatgatgttt aattgagttt gaaattgaac    60
ctgttgcaat gttcggtaat cctaatctgt cgttattcgt rtggattagt cgacgtgttg   120
ctagggttca ttgaacctct atctttgttg acagatcata aattggcttt gaaatgtgta   180
tttctctctc tcgacgattt g    201

<210> SEQ ID NO 23
<211> LENGTH: 201
<212> TYPE: DNA
<213> ORGANISM: Spinacia oleracea

<400> SEQUENCE: 23
attacttcta gttgctcttg tttgctgcat ttaatttgga caatctttgt aatataatta    60
aattagtagg tgtaattgcg tcgccaatac actaacatga racactatgg agaaccatgc   120
aaatagtgag atctaaagtg tgaaattctg gtaatgatgc ggtttgttca cctgattttc   180
acttattttt tcttagcttg a    201

<210> SEQ ID NO 24
<211> LENGTH: 201
<212> TYPE: DNA
<213> ORGANISM: Spinacia oleracea

<400> SEQUENCE: 24
ttaaagagac atactattat actattccga acagagaggg aaaggacggc ggttttttga    60
acagggaagg gaacgtcggc ggttttaggg tggccggtgg ygacagtttt aagtggtcgt   120
ggcgacggtt ttttttaatgt ggcatcaatt tttgggtggc cggtggcggc ggtgttgatg   180
gtcggataaa acagggaaga g    201

<210> SEQ ID NO 25
<211> LENGTH: 201
<212> TYPE: DNA
<213> ORGANISM: Spinacia oleracea

<400> SEQUENCE: 25
atacagtatg ttaatcgtca tccctcttct tattttgtc tctattcttt cttatatctc    60

```
aattatgctt tgtagttgcc tgtgagtatt tcttaaacgt waaagaatac aaacatttca      120
acatcaactc ctaaattttc tggctccatc atatatagca tatactgtat caagtagtgt      180
ttatttttgt cattattgta g                                                201

<210> SEQ ID NO 26
<211> LENGTH: 201
<212> TYPE: DNA
<213> ORGANISM: Spinacia oleracea

<400> SEQUENCE: 26
gaacccatca tcaactgctg ctgtcaaaga caaggttgtt tatgaaaaag acagcggttt       60
tgactcaaag ttacattcag aggcaaagaa aacgctgttt sagatgaact cagatgatct      120
taagggtaca aaagcaggaa agagtggttt gaaagatcta tgtgatgata caagttcgtc      180
ttcttcctct gactttgata t                                                201

<210> SEQ ID NO 27
<211> LENGTH: 201
<212> TYPE: DNA
<213> ORGANISM: Spinacia oleracea

<400> SEQUENCE: 27
tagtttaaaa gttttagatc tttccataaa atcaaacaac acataaaaca atgttgaaac       60
taacaaacaa aaattaggtg tagctcccat aaatttaggg mtgccaaaag aatgggggggc     120 cttggctcag aattagcttt gttgattggc tttttgtaat ttttataaat tattatttct     180
ggatttattt acattttttt a                                                201

<210> SEQ ID NO 28
<211> LENGTH: 201
<212> TYPE: DNA
<213> ORGANISM: Spinacia oleracea

<400> SEQUENCE: 28
agagagagac tgaaaagagc tgcagctgag ttttctttag ctgtatcagt tcctgtttta       60
agtacatgta tcaatggttc aataactcct gattctgcaa ytcttgcttt gatttcttca      120
tttagtgaaa ggttcagaag tgcagtcacg gcatgttctt gtgttatcat cacatcagag      180
tgtaaaagtg taatcaaagg t                                                201
```

SPINACH AND METHOD FOR PRODUCING THE SAME

CROSS REFERENCE TO RELATED APPLICATIONS

The present application is a continuation-in-part application ("CIP application") of U.S. patent application Ser. No. 15/293,639 filed on Oct. 14, 2016 and titled "NOVEL SPINACH AND METHOD FOR PRODUCING THE SAME", which claims priority from Japanese patent application JP 2015-203506 filed on Oct. 15, 2015, the contents of each of which are hereby incorporated by reference.

REFERENCE TO SEQUENCE LISTING SUBMITTED ELECTRONICALLY VIA EFS-WEB

The content of the electronically submitted sequence listing, file name: PH-6655-US-CIP_SEQLIST.TXT; size: 6,709 bytes; and date of creation: Sep. 3, 2020, filed herewith, is incorporated herein by reference in its entirety.

BACKGROUND OF THE INVENTION

Field of the Invention

The present invention relates to a novel spinach line having novel traits that conventional spinach lines do not have, and to a method for producing the same.

Background Art

Spinach (*Spinacia oleracea* L.) is an annual or perennial plant belonging to the genus *Spinacia* of the family Chenopodiaceae, which originated in the West Asia and has been widely cultivated. It is thought that spinach was brought to Japan from China in the 1600s. The roots and leaves (in the rosette form) of this plant are edible. Spinach contains large amounts of vitamins, iron, and calcium, especially in comparison with other vegetables, and it has a very high nutritional value.

The development stages of spinach include the rosette stage, at which rosette leaves develop into an edible vegetable 34 to 40 days after sowing, and the subsequent bolting stage, at which the elongation of stems (bolting) takes place for blooming. In general, for edible spinach, harvest time is the period before the bolting stage. According to "Encyclopedia of Agricultural Techniques, Chapter of Vegetables, vol. 7, Spinach (Basic edition—Spinach: Vegetal characteristics)" (pp. 4-7, Rural Culture Association), the sprouting of spinach takes place 5 to 7 days after sowing, and harvest time is around 30 days after seedling emergence at optimum temperature (15° C. to 20° C.) and around 40 to 100 days at low temperatures. The number of days until harvest would vary significantly depending on temperatures and seasons.

Usages of Spinach are sold and used as fresh product and as an input for processed food production. For spinach used as a fresh product, spinach grown to a height of approximately 10 cm is used for baby leaves, and spinach grown to a height of approximately 20 to 30 cm is used as a grocery produce product. For spinach used as an input for processed food production, spinach grown to a height of approximately 40 to 50 cm is used. For any intended use, excellent yield performance is required.

In addition, "Spinach, Table Beets, and Other Vegetable Chenopods" (V. E. Rubatzky et al., World Vegetable Chapman & Hall, 1997, pp. 457-458) teaches that spinach has hollow petioles at the stage at which its leaves are fully developed. That is, spinach has petioles having a hollow structure at the time of harvesting.

SUMMARY OF THE INVENTION

In the area of spinach line improvement, it has been attempted to reduce the cultivation period by accelerating maturity and to increase the leaf size, the number of leaves, and the thickness of leaves in order to improve yield. Yield performance can be improved with the acquisition of such traits. However, early maturity might excessively accelerate growth unexpectedly, depending on climate conditions, thereby causing a delay in harvesting or making the leaf size greater than the standard shipment size. In other cases, an excessive increase in petiole thickness might cause vegetable quality to decline. These results are problematic. In addition, in the case of a variety with large leaves and a large number of leaves, the leaves become entangled, thereby causing a problem with workability. Therefore, many trial-and-error attempts to increase yield performance have been made.

Moreover, as the production of spinach increases in cold weather periods, damage such as cracks in petioles due to coldness during cultivation—that is, damage to petioles due to so-called cracked stems have been problematic at production sites. Also, during processing spinach into frozen spinach or boiled spinach salad (called "Ohitashi" in Japanese), which has been increasingly prevalent in recent years, the tendency of petioles to crack has been problematic.

In particular, various problems with spinach have occurred at harvest due to hollow petioles. For example, hollow petioles can cause the problem of low yield or the problem of low strength, which may result in snapped petioles or cracked petioles. Therefore, the object of the present invention is to provide a spinach line with the novel feature of solid petioles at harvest and a method for producing a spinach line with the novel feature of solid petioles.

In order to achieve the above object, the present inventor constructed many progeny lines having petioles in which the hollow portion is relatively small over many years. As a result, surprisingly, the present inventor succeeded in constructing a novel spinach line having solid petioles at harvest, such petioles being filled with cells such as parenchyma (sometimes referred to as an "inner medulla"). This has led to the completion of the present invention.

The present invention encompasses the following.

(1) A spinach line, which has solid petioles at harvest time.
(2) The spinach line according to (1), wherein the solidity value (where solidity=100×([total cross-section area]−[void area])/[total cross-section area]) is 80% or greater for the area of a cutting plane that intersects a petiole in the axial direction.
(3) The spinach line according to (1), wherein the solidity value (where solidity=100×([total cross-section area]−[void area])/[total cross-section area]) is 90% or greater for the area of a cutting plane that intersects a petiole in the axial direction.
(4) The spinach line according to (1), wherein the solidity value (where solidity=100×([total cross-section area]−[void area])/[total cross-section area]) is 95% or greater for the area of a cutting plane that intersects a petiole in the axial direction.
(5) The spinach line according to (1), wherein a solid portion extending in the axial direction accounts for 80% or more of a petiole.

(6) The spinach line according to (1), wherein a solid portion extending in the axial direction accounts for 90% or more of a petiole.
(7) The spinach line according to (1), wherein a solid portion extending in the axial direction accounts for 95% or more of a petiole.
(8) The spinach line according to (1), which is of Accession No. FERM BP-22292 or a progeny line of Accession No. FERM BP-22292.
(9) A method for producing spinach seeds, comprising crossing the spinach line according to any one of (1) to (8) with an arbitrary spinach line.
(10) The method for producing spinach seeds according to (9), comprising cultivating seeds obtained by crossing a first spinach line according to any one of (1) to (8) and a second spinach line according to any one of (1) to (8), thereby producing individuals having solid petioles at harvest time.
(11) The method for producing spinach seeds according to (9), comprising crossing a first spinach line according to any one of (1) to (8) and an arbitrary spinach line having hollow petioles at harvest time, thereby producing seeds.
(12) The method for producing spinach seeds according to (11), comprising using a spinach line obtained by cultivating the seeds, thereby selecting individuals with the trait of having solid petioles at harvest time.
(13) Spinach seeds of a line having solid petioles at harvest time obtained by the method for producing spinach seeds according to any one of (9) to (12) or seeds of a progeny line thereof.

Moreover, the present inventor found a causative gene(s) for the phenotype of the solid petioles in genomic DNA using the constructed many progeny lines. This has also led to the completion of the present invention.

The present invention encompasses the following.
(I) A spinach line, which has solid petioles at harvest time and comprising a causative gene(s) for the phenotype of the solid petioles, wherein the causative gene(s) is located between chr1_8757336 and chr1_8797298 on a genome, wherein chr1_8757336 is a SNP of A and G located on 101st position on SEQ ID NO: 24 and wherein chr1_8797298 is a SNP of G and C located on 101st position on SEQ ID NO: 26.
(II) The spinach line according to (I), wherein the causative gene(s) is located closed to chr1-8786706, wherein chr1-8786706 is a SNP of A and T located on 101st position on SEQ ID NO: 25.
(III) The spinach line according to (I), wherein each solid petiole being a petiole having a hollow portion centered in a pith of petiole and having a solid portion surrounding the hollow portion; wherein each hollow portion is smaller than the hollow portion of a conventional spinach plant as measured by a degree of solidity of 80% or greater for the petiole being calculated by 100×([total cross section area]−[void area])/[total cross section area]) for the area of a cutting plane that intersects a petiole in the axial direction of the petiole.
(IV) The spinach line according to (III), wherein the degree of solidity is 90% or greater.
(V) The spinach line according to (III), wherein the degree of solidity is 95% or greater.
(VI) The spinach line according to (I), further comprising a plurality of laminas and a plurality of petioles, each lamina having a lamina base and each petiole having a petiole base: wherein each solid portion optionally has a irregular voids separate from the hollow portion, the irregular voids when present result in the solid portion accounts for 80% or more of a petiole extending in the axial direction between the petiole base and the lamina base of the solid petiole.
(VII) The spinach line according to (VI), wherein the solid portion accounts for 90% or more of a petiole.
(VIII) The spinach line according to (VI), wherein the solid portion accounts for 95% or more of a petiole.
(IX) The spinach line according to (I), which is of Accession No. FERM BP-22292 or a progeny line of Accession No. FERM BP-22292.
(X) A method for producing spinach seeds, comprising crossing the spinach line according to (I) with an arbitrary spinach line.
(XI) The method for producing spinach seeds according to (X), further comprising cultivating seeds obtained by crossing a first spinach line according to (I) and a second spinach line according to (I), thereby producing individuals having solid petioles at harvest time.
(XII) The method for producing spinach seeds according to (X), comprising crossing a first spinach line according to (I) and an arbitrary spinach line having hollow petioles at harvest time, thereby producing seeds.

Effect of the Invention

The spinach line of the present invention has the novel feature of having solid petioles at harvest time, and this feature differs from the features of conventional spinach lines. Therefore, the spinach line of the present invention is superior in terms of yield performance to conventional spinach lines having hollow petioles, and there are no problems such as snapped petioles or petioles having cracks attributed to hollow petioles, resulting in high quality.

Further, according to the spinach production method of the present invention, spinach having the feature of having solid petioles at harvest time can be produced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

The spinach line and spinach production method of the present invention are described in detail below.

The spinach line of the present invention is a plant characterized by the feature of having solid petioles at harvest time. The expression "the spinach line of the present invention" means both a plant of the genus *Spinacia* of the family Chenopodiaceae having the aforementioned feature and a hybrid plant of the genus *Spinacia* of the family Chenopodiaceae having the aforementioned feature and other plants, such as plants belonging to the family Chenopodiaceae. Examples of plants belonging to the family Chenopodiaceae include plants belonging to the genus *Spinacia* of the family Chenopodiaceae, the genus Beta of the family Chenopodiaceae, or the genus *Chenopodium* of the family Chenopodiaceae. The spinach line of the present invention also includes such hybrid plant if it has the feature of having solid petioles at harvest time.

In addition, the whole or a part of a plant of the spinach line of the present invention may be used. That is, the spinach line of the present invention encompasses the entire plant of spinach characterized by the feature of having solid petioles at harvest time, the aerial part of such spinach, and tissues or organs of such spinach. Further, the spinach line of the present invention also encompasses cell(s) obtained from a tissue or organ of spinach characterized by the feature of having solid petioles at harvest time. Examples of such tissues or organs include plant embryos, meristems, calli, pollen, leaves, anthers, stalks, petioles, roots, root tips, fruits, seeds, flowers, cotyledons, and hypocotyls.

The expression "having solid petioles" used herein means a state in which petioles have a hollow portion that is significantly smaller than the hollow portions of petioles of conventional types of spinach, or, preferably, have substantially no hollow portion. When petioles of conventional types of spinach are cut so that the cutting plane (i.e., the transverse plane) intersects with the axial direction, a cortex is present as the outermost portion, a pith consisting of parenchyma is present inside the cortex, and the hollow portion is present at the center of the pith, in general. In addition, several vascular bundles are aligned in the pith. The pith consists of parenchyma, and the hollow portion is formed in petioles as the petioles grow. Therefore, substantially, the hollow portion is formed at center of petioles during the growth of conventional types of spinach.

Figure 1:
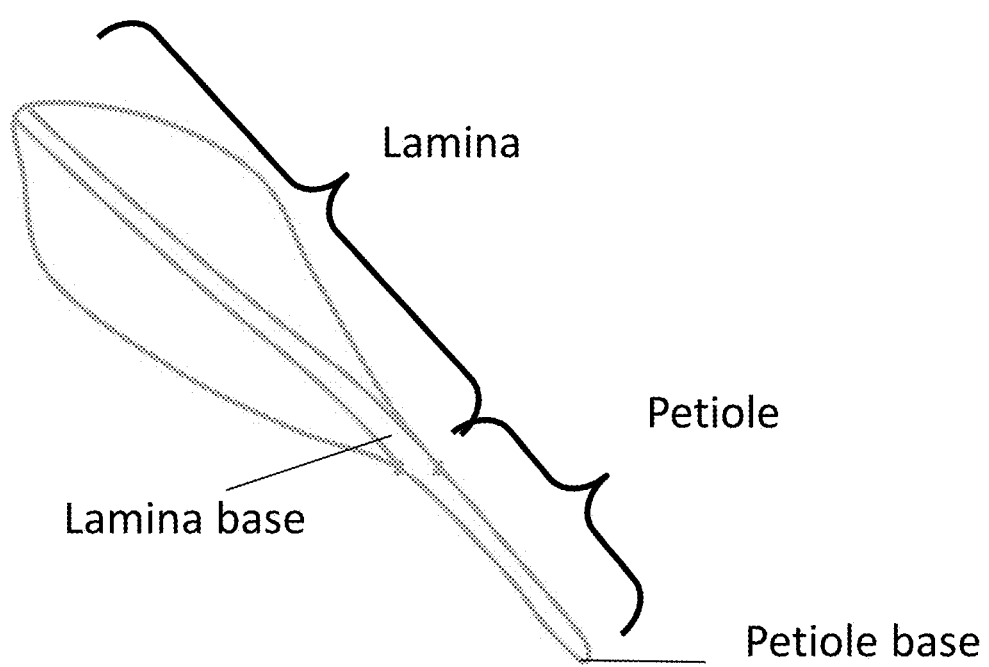
FIG. 1 schematically shows a spinach leaf.

In the case of the spinach line of the present invention, the parenchyma remains in the pith, and thus the solid state is maintained without the formation of a hollow portion, even after petioles have grown to their size at harvest time. Here, FIG. 1 schematically shows spinach including petiole and lamina portions. As described above, the spinach line of the present invention does not have a hollow portion that is formed between the petiole base and the lamina. The spinach line of the present invention may have irregular voids other than such hollow portion being formed in petioles, or may have partially hollow portions in petioles.

Further, the state of "having solid petioles" can be defined based on the area of tissues or organs in a cutting plane obtained by cutting petiole in a direction that intersects with the axial direction. For example, the state of "having solid petioles" can be defined based on a degree of solidity where the degree of solidity is the percentage of area of tissues or organs in the cutting plane. In one example, the degree of solidity can be calculated by the formula: [the degree of solidity]=100×([total cross-section area]−[void area])/[total cross-section area]. When a cutting plane of petioles has the degree of solidity of 80% or greater, the petioles can be defined as solid petioles. Alternatively, a state of solid petioles can be defined as a state in which the degree is 85% or greater, 90% or greater, 95% or greater, 98% or greater, or 99% or greater.

In addition, when the degree of solidity is calculated, the cutting planes of petioles are not particularly limited; however, it is preferable to obtain a cutting plane by cutting a petiole along its transverse plane that is perpendicular or substantially perpendicular to the axial direction. Further, the method employed for determining the total area and the void area in the cutting plane is not particularly limited. Thus, such areas may be determined by visually observing the cutting plane, using a photographed image of the cutting plane, or using graphic data from the cutting plane and graphic image processing software.

Furthermore, the spinach line of the present invention may have petioles in which irregular voids are partially formed, differing from the hollow portion formed between the petiole base and the lamina described above. In such case, based on the spinach line of the present invention, the percentage figure for the petiole area accounted for solid portion in the length of the petiole in the axial direction is preferably 80% or greater, more preferably 90% or greater, and most preferably 95% or greater. Note that the length of a petiole in the axial direction refers to the length between the petiole base and the lamina base.

Moreover, the "harvest time" is defined as the period after the growth stage of spinach at which the plant height (the height between the ground level and the highest point of the plant) reaches 15 cm or more or the length of the longest petiole reaches 5 cm or more and before the bolting stage at which the stretching growth of stems (bolting) takes place for blooming.

In some cases, spinach at harvest time as defined above has fresh leaves that are 3 cm and less in length and have recently grown outward from the center portion. Fresh leaves can be solid not only in the case of the spinach line of the present invention but also in the case of conventional spinach. Therefore, the feature of having solid petioles at harvest time of the spinach line of the present invention is a novel feature observed in leaves other than fresh leaves, and such feature can be distinguished from the features of conventional spinach.

As an aside, the spinach line of the present invention can be constructed by selecting a variety or line having high degree of solidity from among the existing spinach varieties or lines, sowing self-fertilizing seeds of the selected variety or line so as to grow many progeny lines thereof, and repeatedly selecting individuals with high degree of solidity. As an example, seeds of the spinach line constructed in the Examples below were deposited at the following international depository on Aug. 26, 2015 as Accession No. FERM BP-22292: the NITE Patent Microorganisms Depositary (NPMD) (2-5-8 Kazusakamatari, Kisarazu-shi, Chiba, Japan).

In addition, a novel spinach line can be produced by crossing the spinach line of the present invention with an arbitrary spinach line. The term "arbitrary spinach line" used herein refers to both a spinach line (i.e., a conventional spinach line) with the feature of having hollow petioles at harvest time and a spinach line of the present invention with the feature of having solid petioles at harvest time.

Specifically, seeds obtained by crossing a spinach line of the present invention (the first spinach) and a different spinach line of the present invention (the second spinach) are a spinach line with the hereditary trait of having solid petioles at harvest time. Accordingly, spinach seeds with the feature of having solid petioles at harvest time and the like can be produced. The trait of having solid petioles at harvest time described herein is a recessive trait. Therefore, seeds obtained by crossing the spinach lines of the present invention (the first spinach line and the second spinach line) exhibit the trait of having solid petioles at harvest time as a phenotype.

In addition, a progeny spinach line (with the feature of having hollow petioles at harvest time) carrying a recessive trait of having solid petioles at harvest time can be obtained by crossing a spinach line of the present invention and a spinach line (i.e., a conventional spinach line) with the feature of having hollow petioles at harvest time. The thus obtained progeny spinach line carries a recessive trait of having solid petioles at harvest time, and it can be used for constructing a parent spinach line that exhibits the trait of having solid petioles at harvest time as a phenotype. In this case, the spinach line to be produced preferably has traits which were originally inherited by such spinach having the trait of hollow petioles at harvest time. Alternatively, the progeny line may be constructed by, for example, backcrossing with the use of the obtained F1, its progeny line, and the spinach line of the present invention used as a parent line.

Examples of spinach varieties with the trait of having hollow petioles at harvest time include 'Osiri's', 'Progress', 'Aggressive', 'Chronos', 'Trad 7', 'Mirage', 'Triton', 'Kite', 'Accela', 'Hunter', 'Cyclone', and 'Sunhope 7'.

Moreover, as described in the Examples described below, it is suggested that the trait of having solid petioles at harvest time be derived from a recessive gene (hereinafter referred to as "solidity gene"). Therefore, a hybrid with the feature of having solid petioles at harvest time that is constructed using the spinach line of the present invention has a homozygous solidity gene (i.e., a gene in homozygous form). For example, a hybrid with the feature of having solid petioles at harvest time, which was constructed using a maternal line or a paternal line from the spinach line specified with Accession No. FERM BP-22292 for crossing, is characterized by features such as having a solidity gene in homozygous form.

EXAMPLES

The present invention is described in more detail with reference to the Examples below. However, the scope of the present invention is not limited thereto.

Example 1

In this Example, many lines were constructed by crossing lines with relatively high degree of solidity in the petiole medulla portion and lines held by the inventors. Of the thus obtained lines, lines characterized by higher degree of solidity were selected. The progeny lines thereof were verified in terms of traits such as the size of voids in a petiole.

Specifically, a plurality of collected lines from the gene bank of the N. I. Vavilov Research Institute of Plant Industry (Russia) were sown and grown in October 2003. Of these, some individuals of the Middle-Eastern-derived local spinach variety (No. 153) were found to have petioles with relatively high degree of solidity. This variety was developed to obtain 200 individuals. Among these individuals, those having petioles with relatively high solidity were selected and designated as the "ME" lines. Self-fertilizing seeds of the ME lines were collected so that a progeny line thereof (MEBC1) was obtained.

Next, MEBC1 seeds were sown in 2005. Among 200 grown individuals, only one individual was found to have a petiole medulla portion with 100% of the degree of solidity. This individual was selected. Self-fertilizing seeds were collected therefrom so that MEBC2 was obtained. Then, the obtained MEBC2 seeds was sown and developed. As a result, among 200 grown individuals, the percentage of individuals having 100% of the degree of solidity in the petiole medulla portion increased to about 20%. The seeds obtained from the individuals of MEBC2 were designated MEBC3 seeds.

Then, MEBC3 seeds were sown and developed in 2007. All grown individuals were found to have 100% solidity in the petiole medulla portion. Thus, line A was completed (MEBC3).

In 2007, seeds that had been obtained by crossing line A and a western local variety characterized by dark green round leaves were sown. The resulting F1 hybrid seeds were sown and seedlings were grown. Self-fertilizing seedlings of the line were collected so that F2 seeds were obtained. Then, the F2 seeds were sown and developed. Among 200 grown individuals, individuals having high solidity in petioles were selected. Their progenies were isolated, self-fertilized, and collected. This procedure was repeated for five generations. Accordingly, line B having many fixed traits, including the trait of solidity in petioles and other dominant traits of deep green leaf color and downy mildew resistance was constructed. Also in 2007, line A and a local oriental variety characterized by blade-shaped leaves were crossed. Selection and seed collection were carried out as in the case of line B to select individuals having the trait of high solidity in petioles and the other dominant traits. Accordingly, line C having the above traits as fixed traits was constructed.

Next, lines B and C were crossed as female and male parents, respectively. F1 hybrid seeds thereof were collected to construct a test cross D in 2012. In 2013, 200 individuals of the test cross D were sown to confirm the traits thereof. As a result, all individuals were found to have 100% solidity in petioles.

Seeds of the line C used as a parent of the test cross D obtained above (CHUTOU) were deposited at the following international depository on Aug. 26, 2015 (the test cross D being labeled as "CHUTOU" by the depositor for identification, Accession No. FERM BP-22292): the NITE Patent Microorganisms Depositary (NPMD) (2-5-8 Kazusakamatari, Kisarazu-shi, Chiba, Japan).

As stated above, lines A, B, and C and the test cross D constructed in this Example were confirmed to be spinach lines with the novel feature of having solid petioles at harvest time.

Moreover, as described in this Example, it was necessary to select the recessive trait of having solid petioles, breed lines resistant to conventional diseases and select dominant traits for spinach cultivation, meaning that long-term selection and breeding were necessary. As a result, it took 11 years from 2003 to 2013 to construct the lines.

Example 2

In this Example, first, the CHUTOU line and a line characterized by thick hollow petioles having a thick cortex (SCOPE line) were crossed so that an F1 population was constructed. As a result of examination of petioles of individuals of the F1 population, all petioles were found to be hollow. The results showed that the gene associated with the trait of having solid petioles differs from the gene associated with the trait of having thick petioles.

Also, in this Example, F1 populations of the solid line (CHUTOU line) and the SCOPE line were self-fertilized to construct their F2 progeny lines. Table 1 shows the results obtained by calculating the percentage of F2 individuals having the hollow petiole trait and the percentage of F2 individuals having the solid petiole trait.

TABLE 1

| F2 population | Total number of individuals | Hollow | Solid | Solidity percentage |
|---|---|---|---|---|
| #1 | 70 | 61 | 9 | 12% |
| #2 | 115 | 76 | 39 | 34% |

As shown in Table 1, the results of F2 segregation data suggest that the solidity gene associated with the trait of having solid petioles is a recessive gene. This means that a line having a homozygous solidity gene associated with the trait of having solid petioles has solid petioles, while on the other hand, a line having a heterozygous solidity gene has hollow petioles.

Example 3

In this Example, the test cross D constructed in Example 1 and the control varieties were compared in terms of yield, leaf weight, leaf length, and solidity of the insides of petioles at harvest time. Also, in this Example, sowing was carried out on Oct. 10, 2013, followed by harvesting on Feb. 26, 2014.

Seeds of five lines (the test cross D and control varieties ('Hunter', 'Aspire', 'Progress', and 'Riviera')) were sown and grown until the plant heights reached approximately 25 to 30 cm. Five plants were harvested from each experimental plot to determine weight per plant, 10-leaf weight (determined as the sum of weights of 10 leaves having similar sizes sampled from 5 stocks), and maximum leaf length (determined as the length of the longest leaf of each stock). Table 2 shows the results.

Figure 2:
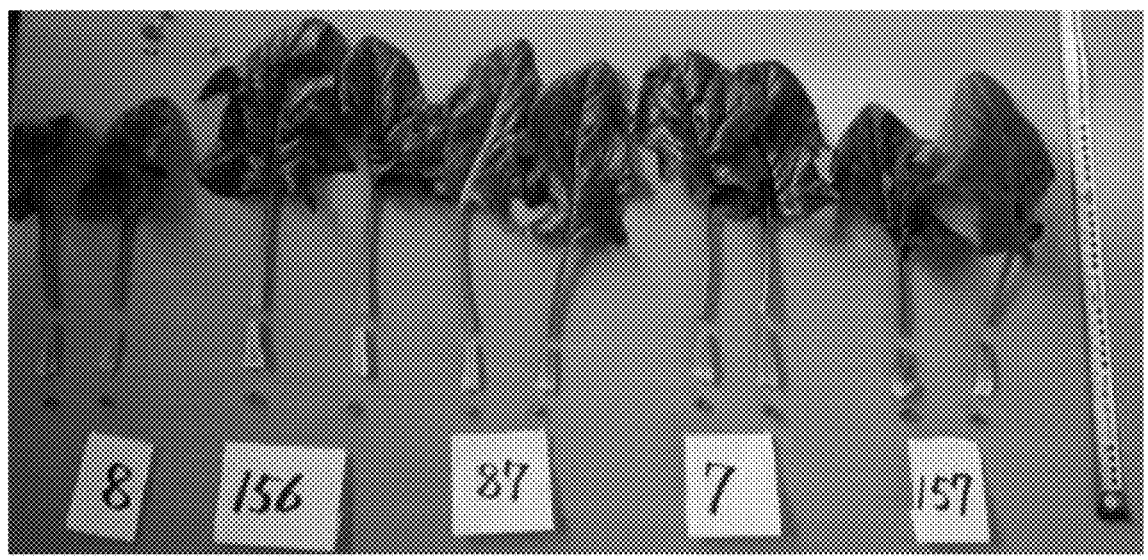
FIG. 2 shows a photographic image of petioles of the test cross D developed in the Examples and the control varieties that were cut so that each cutting plane intersects with the axial direction.

In addition, two average-sized leaves of each of the five lines were aligned and their petioles were cut at the level 4 to 5 cm from the base portion along the direction perpendicular to the extension direction. FIG. 2 shows a photographic image of the leaves of the varieties and the transverse planes thereof for comparison.

Figure 3:
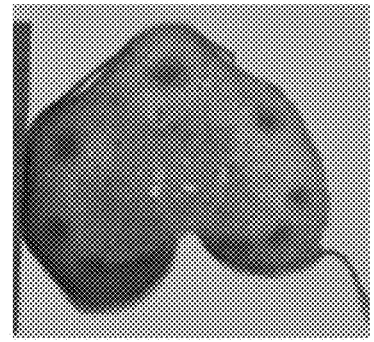
FIG. 3 shows a photographed image of a cutting plane of a petiole of the test cross D constructed in the Examples.
Figure 4:
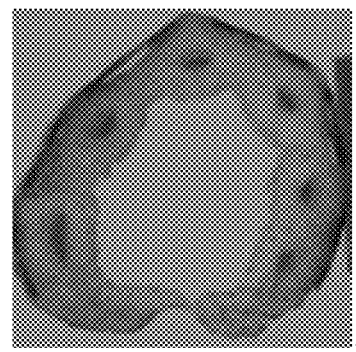
FIG. 4 shows a photographed image of a cutting plane of a petiole of the spinach variety 'Riviera' used as a control line.

Solidity of the petiole medulla portion on each transverse plane (the solid area/the area of the entire transverse plane for each petiole) was determined via Image J. FIGS. 3 and 4 show a cutting plane of the test cross D and a cutting plane of Riviera upon determination, respectively.

TABLE 2

| | Comparative Example Progress | Comparative Example Hunter | Example Test cross D | Comparative Example Aspire | Comparative Example Riviera |
|---|---|---|---|---|---|
| Average weight per plant (g) | 90.2 | 92.6 | 136.2 | 120.0 | 102.8 |
| 10-leaf weight (g) | 92 | 67 | 121 | 102 | 101 |
| Average maximum leaf length (cm) | 27.0 | 23.5 | 31.0 | 33.1 | 27.9 |

TABLE 2-continued

| | Comparative Example Progress | Comparative Example Hunter | Example Test cross D | Comparative Example Aspire | Comparative Example Riviera |
|---|---|---|---|---|---|
| Solidity in petiole medulla portion (%) | 64.4 | 61.0 | 100.0 | 66.0 | 63.9 |

Based on the above, it was found that the largest average maximum leaf length was obtained for 'Aspire' in the Comparative Example, while the highest average weight per plant and 10-leaf weight were obtained for the test cross D constructed in Example 1. Accordingly, it was found that the test cross D is spinach with high yield performance. It was further revealed that the solidity value for the petiole medulla portion for the test cross D was 100%, which was higher than the values of 61.0% to 66.0% for the Comparative Examples.

Table 3 lists determination results for leaves with snapped petioles after harvesting and adjustment.

TABLE 3

| | Comparative Example Progress | Comparative Example Hunter | Example Test cross D |
|---|---|---|---|
| Number of leaves with snapped petioles (Number of leaves) | 9 | 14 | 8 |

As shown in Table 3, test cross D spinach showed a tendency to have fewer leaves with snapped petioles than spinach of the Comparative Examples.

The above results of this Example showed that spinach of the test cross D constructed in Example 1 is superior to conventional spinach in terms of solidity in petioles at harvesting time, and the yield of such spinach as a whole is high.

Example 4

Figure 5:
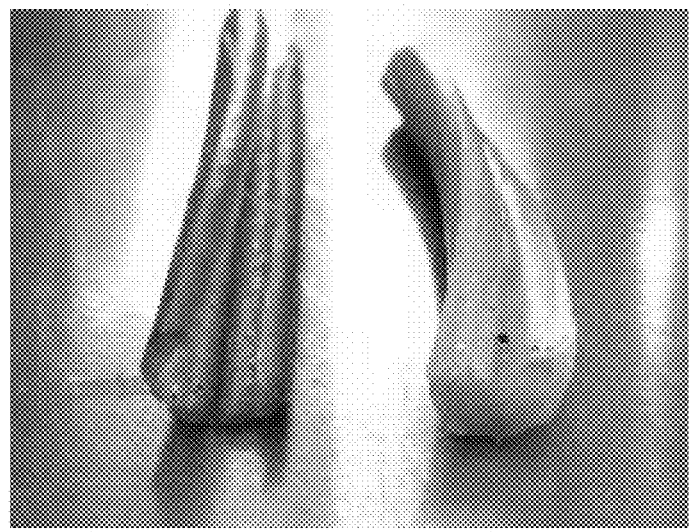
FIG. 5 shows a photographed image of a portion of a petiole of the test cross D constructed in the Examples and that of spinach variety 'Accela'.

In this Example, spinach of the test cross D constructed in Example 1 and spinach of an existing type considered to have thick solid petioles were cultivated and harvested. In the case of 'Accela', which was used as a control for comparison, some petioles were found to have cracks at the time of harvesting, while on the other hand, no cracks were found in petioles of the test cross D (FIG. 5). The two lines were washed with water immediately after harvesting and immersed in boiled water for 1 minute for heat treatment. Then they were immersed in water for 1 minute, followed by water removal. In this Example, sowing was carried out on Apr. 15, 2014, and harvesting and examination were carried out on May 23, 2014.

First, the cutting planes after harvesting were compared. 'Accela', used as a control for comparison, was found to have petioles in which the thickness between the hollow portion and the epidermis of the upper portion of the phylloplane was low, and therefore the petioles were partially thin. Meanwhile, the test cross D constructed in Example 1 was found to have petioles filled with parenchymatous cells, and the epidermis of the upper portion of the phylloplane and petioles were not thin.

Figure 6:
FIG. 6 shows a photographed image of cutting planes of petioles of the test cross D constructed in the Examples and a photographed image of cutting planes of petioles of 'Accela' after heat treatment.
Figure 6:
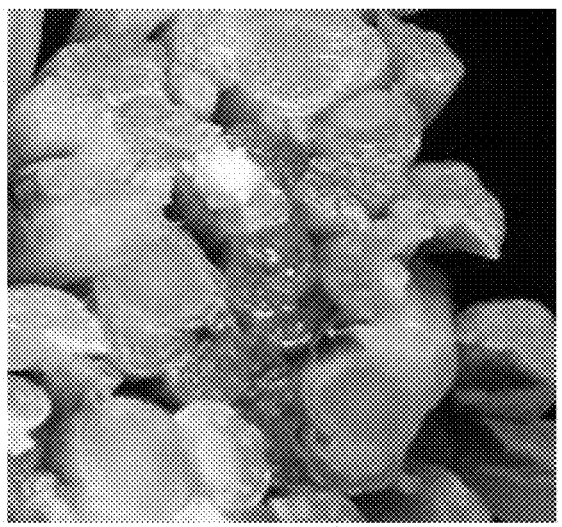

Next, the cutting planes of leaves after heat treatment were compared. As a result, 'Accela', which was used as a control for comparison, was found to have hollow petioles, while on the other hand, the test cross D constructed in Example 1 was found to have petioles that were all solid inside (FIG. 6). Note that the photographed image of 'Accela' shown in FIG. 6 shows some petioles in which the hollow portion appears to have collapsed due to squeezing for water removal after heat treatment. The texture of petioles after heat treatment was strong for 'Accela', which was used as a control for comparison. On the other hand, the texture was relatively soft and smooth for the test cross D constructed in Example 1. These results revealed that spinach of the test cross D constructed in Example 1 has a characteristic texture that is relatively softer than the texture of conventionally known spinach.

Example 5

In this Example. in order to identify the locus position of the causative gene which causes the phenotype of solid petioles at harvest time, genetic analysis was carried out by the following method.
Materials and Methods The F2 segregation populations of the solid line (CHUTOU-2) and the hollow line (CHUKU) were seeded and cultivated until the harvesting time. The solid line CHUTOU-2 used for the genetic analysis is a line whose parents lines are identical to those of the deposited line (CHUTOU, Example 1), and there is no difference from the deposited line in the genetic background and the genetic region related to the phenotype of solid petioles.

The 317 individuals of the F2 population were examined for solid and hollow phenotypes in axially intersecting cut planes of petioles according to the Examples 1 and 2. Phenotypic studies revealed that 75 individuals fulfilled the condition of solid petioles according to the examples and 242 individuals fulfilled the condition of hollow petioles. In the F2 population, approximately ¼ of the individuals show solid petioles phenotypes, so we inferred that the causative gene causing the solid petioles was a recessive gene.

Based on the above analysis, it is estimated that the genotype of the causative gene region is homozygous for the recessive gene (a/a) in individuals exhibiting solid petioles phenotypes, whereas the genotype of the causative gene region is likely to have homozygous for the dominant gene (A/A) or heterozygous for the dominant gene and the recessive gene (A/a) in individuals exhibiting hollow petioles phenotypes.

A high proportion of individuals (in this case, individuals exhibiting hollow petioles phenotypes) in the sample population who are unable to estimate the correct genotype in the linkage analysis may adversely affect the accuracy of the analysis. Considering this fact, the population for linkage analysis was constructed so that the proportion of individuals showing solid petioles phenotypes was as large as possible. Of the 317 individuals whose traits were examined, a total of 183 individuals consisting of 75 individuals showing solid petioles phenotypes and 108 individuals showing hollow petioles phenotypes constructed as described above were used as a linkage analysis population, and genomic DNA was extracted.

We performed genotyping using the DNA of a population for the linkage analysis and the SNP marker (KASP) designed on the Spinach Genome (Spinach genome sequence (v1)) published in SpinachBase (http://www.spinachbase.org/).

Table 4 shows examples of KASP markers used for genotyping.

TABLE 4

| chromosome | physical position Spinach genome sequence position (v1) | Direction on ref. | KASP primer | allele of the primers | KASP primer Sequence (5'→3') | SEQ ID NO: |
|---|---|---|---|---|---|---|
| chr1 | 8733953 | Reverse strand | allele specific primer_1<br>allele specific primer_2<br>common primer | F allele<br>H allele | GAAGGTGACCAAGTTCATGCTGCAACACGTCGACTAATCCAC<br>GAAGGTCGGAGTCAACACGATTGCAACACGTCGACTAATCCAT<br>GAACCTGTTGCAATGTTCGGT | SEQ ID NO: 1<br>SEQ ID NO: 2<br>SEQ ID NO: 3 |
| chr1 | 8747983 | Forward strand | allele specific primer_1<br>allele specific primer_2<br>common primer | H allele<br>F allele | GAAGGTGACCAAGTTCATGCTCGTCGCCAATACACTAACATGAA<br>GAAGGTCGGAGTCAACGGATTCGTCGCCAATACACTAACATGAG<br>CAGGTGAACAAACCGCATCAT | SEQ ID NO: 4<br>SEQ ID NO: 5<br>SEQ ID NO: 6 |
| chr1 | 8757336 | Reverse strand | allele specific primer_1<br>allele specific primer_2<br>common primer | F allele<br>H allele | GAAGGTGACCAAGTTCATGCTCCACGACCACTTAAAACTGTCA<br>GAAGGTCGGAGTCAACGGATTCCACGACCACTTAAAACTGTCG<br>GAACAGAGAGGGAAAGGACGG | SEQ ID NO: 7<br>SEQ ID NO: 8<br>SEQ ID NO: 9 |
| chr1 | 8786706 | Forward strand | allele specific primer_1<br>allele specific primer_2<br>common primer | F allele<br>H allele | GAAGGTGACCAAGTTCATGCTTGCCTGTGAGTATTTCTTAAACGTA<br>GAAGGTCGGAGTCAACGGATTGCCTGTGAGTATTTCTTAAACGTT<br>TGGAGCCAGAAAATTTAGGAGTTG | SEQ ID NO: 10<br>SEQ ID NO: 11<br>SEQ ID NO: 12 |
| chr1 | 8797298 | Reverse strand | allele specific primer_1<br>allele specific primer_2<br>common primer | H allele<br>F allele | GAAGGTGACCAAGTTCATGCTCCCTTAAGATCATCTGAGTTCATCTG<br>GAAGGTCGGAGTCAACGGATTCCCTTAAGATCATCTGAGTTCATCTC<br>TCAGAGGCAAAGAAAACGCTG | SEQ ID NO: 13<br>SEQ ID NO: 14<br>SEQ ID NO: 15 |
| chr1 | 8800403 | Forward strand | allele specific primer_1<br>allele specific primer_2<br>common primer | F allele<br>H allele | GAAGGTGACCAAGTTCATGCTTGTAGCTCCCATAAATTTAGGGC<br>GAAGGTCGGAGTCAACGGATTTGTAGCTCCCATAAATTTAGGGA<br>AGCTAATTCTGAGCCAAGGCC | SEQ ID NO: 16<br>SEQ ID NO: 17<br>SEQ ID NO: 18 |
| chr1 | 8838391 | Forward strand | allele specific primer_1<br>allele specific primer_2<br>common primer | H allele<br>F allele | GAAGGTGACCAAGTTCATGCTGTTCAATAACTCCTGATTCTGCAAC<br>GAAGGTCGGAGTCAACGGATTGTTCAATAACTCCTGATTCTGCAAT<br>CACAAGAACATGCCGTGACTG | SEQ ID NO: 19<br>SEQ ID NO: 20<br>SEQ ID NO: 21 |

One base at the 3' end in the sequences of allele specific primer_1 and allele specific primer_2 of each marker corresponds to the SNP position. In table 4, the term "H allele" indicates a hollow petioles type; "F allele" indicates a solid petioles type. For example, CHUTOU-2 has homozygous for F allele, "T", in the sequence of chr1-8838391. Similarly, CHUTOU-2 has homozygous for H allele, "C", in the sequence of chr1-8838391. In addition, in F1 of CHUTOU-2 and CHUKU, the sequence of chr1-8838391 is "T/C", and F1 has heterozygous for F allele and H allele. Using the above genomic DNA and KASP markers, the genotype of each SNP can be conveniently investigated in the linkage analysis population.

KASP primers, allele specific primer_1 and allele specific primer_2, each includes a tail region consisting of 21 nucleotides from 5' end thereof and an allele specific region consisting of remaining nucleotides (i.e. 21-26 nucleotides of 3' end). As described above, the 3'end of the allele specific region corresponds to a target SNP. Accordingly, in the KASP method, a specific region including a target SNP, such as chr1-8838391, is amplified by allele specific primer_1 or allele specific primer_2 and a common primer (see table 4).

Therefore, KASP markers listed in table 4, such as chr1-8733953, chr-8838391 or so on, can be defined a specific position in the amplified region (the amplified DNA fragment). Here, the amplified regions comprising KASP markers listed in table 4 can be identified by sequencing analysis using obtained DNA fragments in the KASP method, or by searching the Spinach Genome (Spinach genome sequence (v1)) published in SpinachBase.

In addition, with the use of the Spinach Genome (Spinach genome sequence (v1)) published in SpinachBase, KASP markers listed in table 4 can be defined a specific position of in a genomic region. Specifically, by searching the Spinach Genome (Spinach genome sequence (v1)) using sequences of allele specific regions of KASP primers, chr1-8733953 is found to be located on 101st position on SEQ ID NO: 22; chr1-8747983 is found to be located on 101st position on SEQ ID NO: 23; chr1-8757336 is found to be located on 101st position on SEQ ID NO: 24; chr1-8786706 is found to be located on 101st position on SEQ ID NO: 25; chr1-8797298 is found to be located on 101st position on SEQ ID NO: 26; chr1-8800403 is found to be located on 101st position on SEQ ID NO:27; chr1-8838391 is found to be located on 101st position on SEQ ID NO:28.

Therefore, KASP markers listed in table 4 can be defined by SEQ ID NOs: 22 to 28. That is, chr1-8733953 is a SNP of G and A located on 101st position on SEQ ID NO:22; chr1-8747983 is a SNP of A and G located on 101st position on SEQ ID NO:23; chr1-8757336 is a SNP of T and C located on 101st position on SEQ ID NO:24; chr1-8786706 is a SNP of A and T located on 101st position on SEQ ID NO:25; chr1-8797298 is a SNP of G and C located on 101st position on SEQ ID NO:26; chr1-8800403 is a SNP of C and A located on 101st position on SEQ ID NO:27; chr1-8838391 is a SNP of C and T located on 101st position on SEQ ID NO:28.

It should be noted that each of SEQ ID NOs: 22 to 28 is a part of the genomic DNA sequence stored in the database as a reference sequence of Spinach. Therefore, the positions of KASP markers detected by sequencing analysis using obtained DNA fragments in the KASP method may different from those in SEQ ID NOs: 22 to 28.

Alternatively, KASP markers listed in table 4 can be defined by nucleotide sequence of the allele specific region in KASP primers (allele specific primer_1 and allele specific primer_2). As described above, since the allele specific region in KASP primers is a genomic region including a target SNP, therefore, KASP markers are defined as a nucleotide at the 3' end of the allele specific region.

After obtaining Genotyping data, the linkage analysis using AntMAP Ver. 1.1 (Iwata H, Ninomiya S, Breeding Science, 2006, Volume 56, Issue 4, Pages 371-377) (http://lbm.ab.a.u-tokyo.ac.jp/~iwata/antmap/) was performed. For the linkage analysis, criterion of Grouping was changed to Distance (cM)/Haldane/Threshold0.9, otherwise defaults were set.

Results

Table 5 shows the genotypes of seven individuals (Sample No. 25/68/70/45/48/51/172) that have undergone recombination in the peripheral regions of the causative gene based on the results of genotyping using KASP markers shown in Table 4, and shows the phenotypes thereof. In the table 5, "A" indicates CHUKU allele and "B" indicates CHUTOU-2 allele. For example, B/B indicates that the individual has homozygous for F allele of CHUTOU-2. A/B indicates that the individual has heterozygous for both F allele and H allele.

TABLE 5

| Sample No. | 25 | 68 | 70 | 45 | 48 | 51 | 172 | Distance (cM) |
|---|---|---|---|---|---|---|---|---|
| Phenotype (F: Solid, H: Hollow) | F | F | F | F | F | F | H | 1.6 |
| chr1_8733953 | B/B | B/B | B/B | A/B | A/B | A/B | B/B | 0.0 |
| chr1_8747983 | B/B | B/B | B/B | A/B | A/B | B/B | B/B | 0.3 |
| chr1_8757336 | B/B | B/B | B/B | A/B | A/B | B/B | A/B | 1.1 |
| chr1_8786706 | B/B | B/B | B/B | B/B | B/B | B/B | A/B | 1.6 |
| chr1_8797298 | B/B | B/B | A/B | B/B | B/B | B/B | A/B | 2.2 |
| chr1_8800403 | A/B | A/B | A/B | B/B | B/B | B/B | A/B | 3.0 |
| chr1_8838391 | A/B | A/B | A/B | B/B | B/B | B/B | A/B | 3.3 |

According to the table 5, in the SNP of chr1-8786706, 6 individuals of Sample No. 25/68/70/45/48/51 with genotype B/B show phenotype F (solid petioles), and Sample No. 172 with genotype A/B show phenotype H (hollow petioles), indicating that this SNP is highly correlated with the phenotype.

Figure 7:
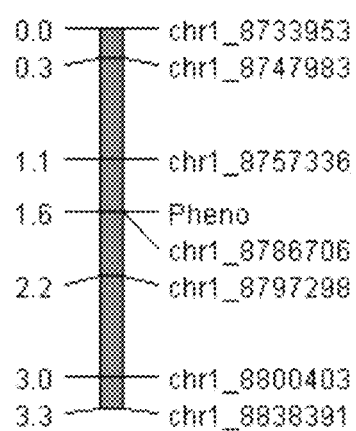
FIG. 7 shows a linkage map of a part of chromosome 1.

Linkage analysis revealed that the causative gene (or genes) that causes (or cause) solid petioles was (or were) located within the range between chr1_8757336 and chr1_8797298 on the reference genomes (Spinach genome sequence (v1)) published in SpinachBase. Especially, it is revealed that the SNP of chr1_8786706 was linked at a genetic distance of 0 cM (FIG. 7, Table 2).

In conclusion, according to this example, the causative gene (or genes) involved in solid petioles is located between chr1_8757336 and chr1_8797298 in a genomic DNA, wherein chr1_8757336 is a SNP located on 101st position on SEQ ID NO: 24 and wherein chr1_8797298 is a SNP located on 101st position on SEQ ID NO: 26. Here, chr1_8757336 may have T or C in the reference genome; chr1_8797298 may have G or C in the reference genome.

In addition, according to this example, the causative gene (or genes) involved in solid petioles is located close to chr1-8786706, wherein chr1-8786706 is a SNP located on 101st position on SEQ ID NO: 25. Here, chr1-8786706 may have A or T in the reference genome.

In the meanwhile, KASP markers used for the above linkage analysis were used for the purpose of specifying the locus position of the causative gene. These KASP markers can be used for DNA markers to select spinach having a solid petioles phenotype. However, DNA markers to select spinach having a solid petioles phenotype are not limited to these KASP markers. Other SNPs (e.g. other KASP markers), which highly link to the solid petioles phenotype, can be used as DNA markers to select spinach having a solid petioles phenotype.

What is claimed is:

1. A spinach line, which has solid petioles at harvest time and comprising a causative gene(s) for the phenotype of the solid petioles, wherein the causative gene(s) is located between chr1_8757336 and chr1_8797298 on a genome, wherein chr1_8757336 is a SNP located on 101st position on SEQ ID NO: 24 and wherein chr1_8797298 is a SNP of located on 101st position on SEQ ID NO: 26, and wherein the causative gene(s) is present in a spinach plant, grown from representative seed deposited under Accession No. FERM BP-22292.

2. The spinach line according to claim 1, wherein the causative gene(s) is located proximal to chr1_8786706, wherein chr1_8786706 is a SNP located on 101st position on SEQ ID NO: 25.

3. The spinach line according to claim 1, wherein each solid petiole being a petiole having a hollow portion centered in a pith of petiole and having a solid portion surrounding the hollow portion;

wherein each hollow portion is smaller than the hollow portion of a conventional spinach plant as measured by a degree of solidity of 80% or greater for the petiole being calculated by 100×([total cross section area]−[void area])/[total cross section area]) for the area of a cutting plane that intersects a petiole in the axial direction of the petiole.

4. The spinach line according to claim 3, wherein the degree of solidity is 90% or greater.

5. The spinach line according to claim 3, wherein the degree of solidity is 95% or greater.

6. The spinach line according to claim 1, further comprising a plurality of laminas and a plurality of petioles, each lamina having a lamina base and each petiole having a petiole base:

wherein each solid portion optionally has a irregular voids separate from the hollow portion, the irregular voids when present result in the solid portion accounts for 80% or more of a petiole extending in the axial direction between the petiole base and the lamina base of the solid petiole.

7. The spinach line according to claim 6, wherein the solid portion accounts for 90% or more of a petiole.

8. The spinach line according to claim 6, wherein the solid portion accounts for 95% or more of a petiole.

9. The spinach line according to claim 1, which is of Accession No. FERM BP-22292 or a progeny line of Accession No. FERM BP-22292.

10. A method for producing spinach seeds, comprising crossing the spinach line according to claim 1 with an arbitrary spinach line.

11. The method for producing spinach seeds according to claim 10, further comprising cultivating seeds obtained by crossing a first spinach line and a second spinach line which has solid petioles at harvest time and comprising a causative gene(s) for the phenotype of the solid petioles,
- wherein the causative gene(s) is located between chr1_8757336 and chr1_8797298 on a genome,
- wherein chr1_8757336 is a SNP located on 101st position on SEQ ID NO: 24 and wherein chr1_8797298 is a SNP of located on 101st position on SEQ ID NO: 26, thereby producing individuals having solid petioles at harvest time.

12. The method for producing spinach seeds according to claim 10, comprising crossing a first spinach line which has solid petioles at harvest time and comprising a causative gene(s) for the phenotype of the solid petioles,
- wherein the causative gene(s) is located between chr1_8757336 and chr1_8797298 on a genome,
- wherein chr1_8757336 is a SNP located on 101st position on SEQ ID NO: 24 and wherein chr1_8797298 is a SNP of located on 101st position on SEQ ID NO: 26, and
- an arbitrary spinach line having hollow petioles at harvest time, thereby producing seeds.

13. The method for producing spinach seeds according to claim 12, further comprising cultivating the seeds and selecting individual plants with the trait of having solid petioles at harvest time.

14. Spinach seeds of a line having solid petioles at harvest time obtained by the method for producing spinach seeds according to claim 10 or seeds of a progeny line thereof.

* * * * *